United States Patent [19]

Smith et al.

[11] Patent Number: 5,297,441
[45] Date of Patent: Mar. 29, 1994

[54] APPARATUS FOR SUPPORTING A TEST SPECIMEN FOR COMPRESSION TESTING

[75] Inventors: Gregory J. Smith, Kent; Stephen H. Ward, Seattle; Ronald F. Zabora, Kent, all of Wash.

[73] Assignee: The Boeing Company, Seattle, Wash.

[21] Appl. No.: 929,226

[22] Filed: Aug. 14, 1992

[51] Int. Cl.⁵ ............................................. G01N 3/04
[52] U.S. Cl. ..................................... 73/860; 73/818
[58] Field of Search .............. 73/818, 819, 820, 821, 73/822, 823, 825, 856, 859, 860

[56] References Cited

U.S. PATENT DOCUMENTS

| | | | |
|---|---|---|---|
| 683,184 | 9/1901 | Rockwell | 269/37 X |
| 2,350,060 | 5/1944 | Montgomery | 265/12 |
| 2,368,900 | 2/1945 | Templin . | |
| 2,460,679 | 2/1949 | Clay | 269/110 X |
| 2,500,068 | 3/1950 | Gerard . | |
| 3,457,828 | 7/1969 | Durham | 90/11 |
| 3,559,473 | 2/1971 | Dudderar et al. | 73/818 |
| 4,840,070 | 6/1989 | Ralfs et al. | 73/818 |
| 4,850,231 | 7/1989 | Ralfs et al. | 73/859 |

Primary Examiner—Jerry W. Myracle
Attorney, Agent, or Firm—R. H. Sproule

[57] ABSTRACT

Apparatus for stabilizing a test specimen in a compression/tension testing machine. The apparatus supports the test piece along its lengthwise edge or edges to prevent unwanted Euler buckling, however in a manner so as not to prevent sublaminate buckling. In one embodiment the apparatus supports the test piece along both of its lengthwise edges while engaged between the grips of the test machine. In a second embodiment, the apparatus supports the test piece along only one of its lengthwise edges. In a third embodiment, the apparatus includes grip plates which are mounted to the test machine and which engage a portion of the test specimen while the remainder of the specimen is supported along its lengthwise edges by stabilizer plates.

2 Claims, 5 Drawing Sheets

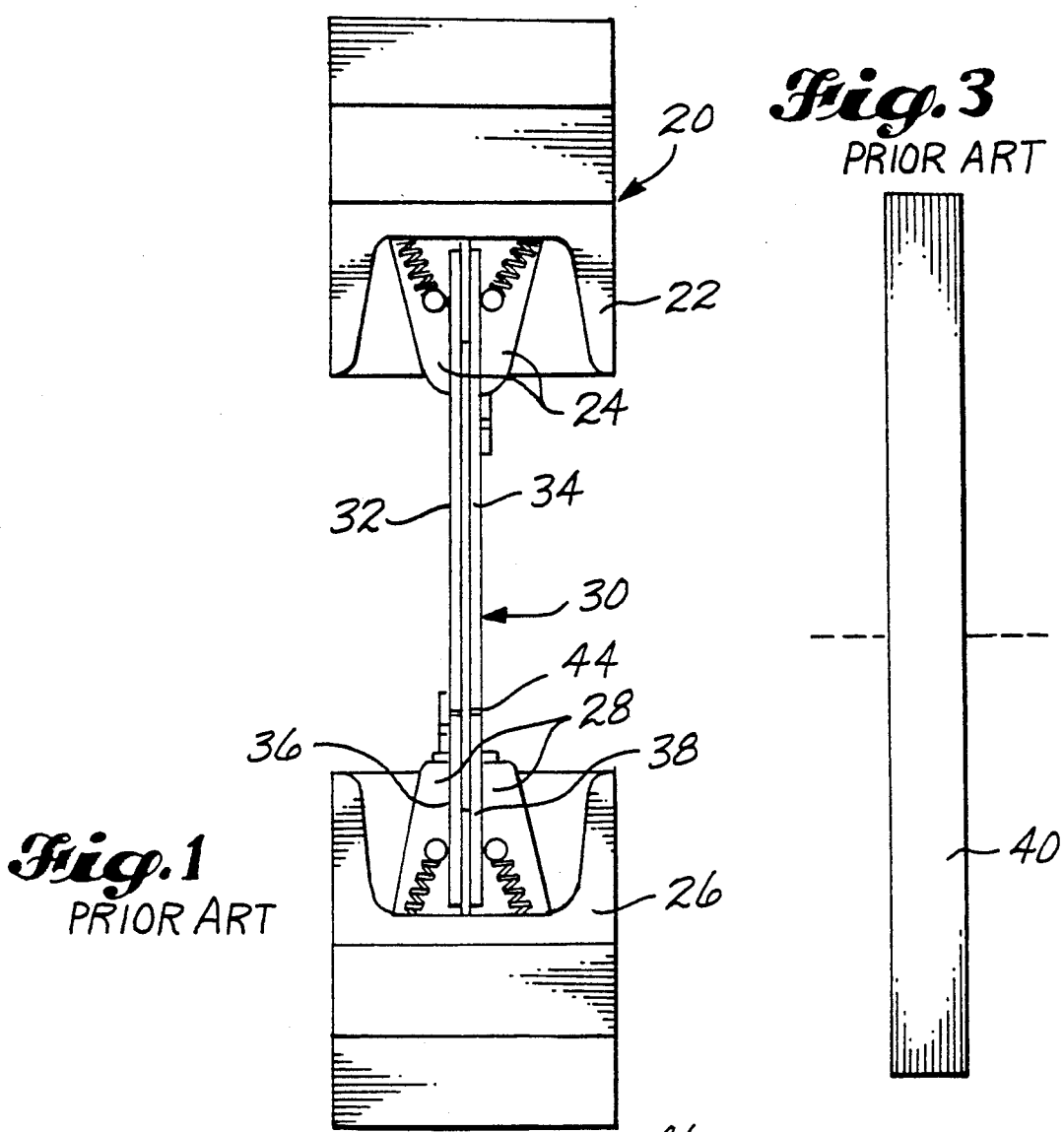
Fig. 1 PRIOR ART
Fig. 3 PRIOR ART
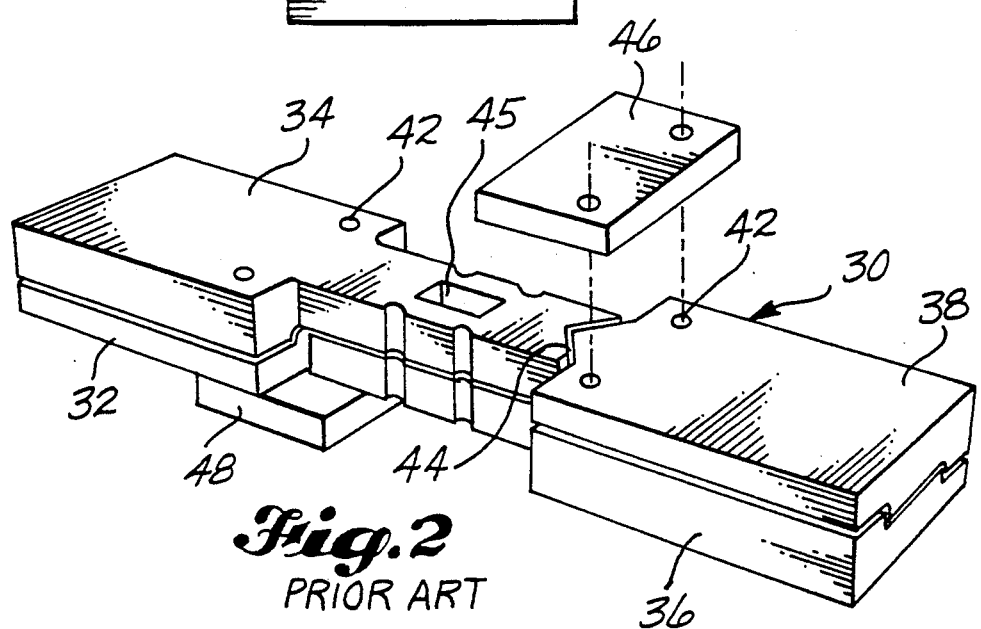
Fig. 2 PRIOR ART

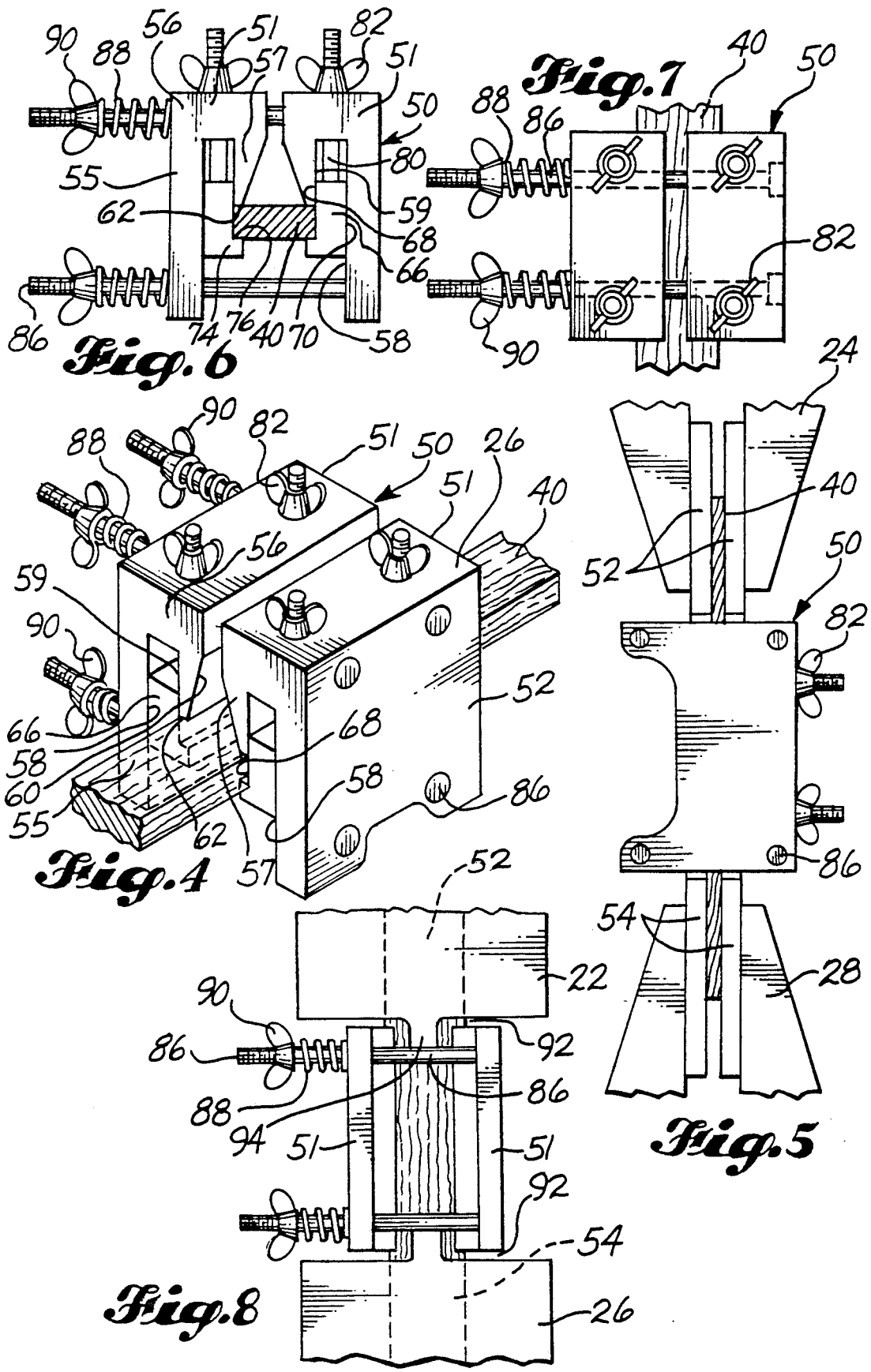

APPARATUS FOR SUPPORTING A TEST SPECIMEN FOR COMPRESSION TESTING

TECHNICAL FIELD

The present invention pertains to apparatus for supporting a specimen for compression testing the specimen.

BACKGROUND OF THE INVENTION

When manufacturing various parts it is desirable to test the parts themselves or certain specimens from these parts for mechanical strength. For example, in the airplane industry, some of the airplane parts are made out of composite materials. It is desirable to test specimens of these parts for compression strength.

There are large machines available to accomplish this testing. For example, during compression testing, the specimen, such as a flat piece of laminate (sometimes referred to as a "coupon"), is supported by a conventional test specimen holder (also referred to as a "fixture") between the grips of the testing machine. The machine compresses the coupon in a lengthwise direction until it fractures whereupon the machine provides a readout of the force required to fracture the coupon. Support for the coupon along its lengthwise axis is required during compression testing to prevent Euler column buckling. However the coupon should be supported in a manner so that sublaminate buckling of the specimen or any natural failure mode of interest is not restricted. In addition, during the compression testing it is sometimes desirable to attach a extensometer (or strain gauge) to the coupon to measure the amount of deformation of the coupon during compression.

Existing -compression fixtures support t faces of the test specimen. While these fixtures restrict the Euler column buckling they also restrict the valid sublaminate buckling failure mode. Specimen designs based on stable column sections have been used to measure compression properties of composites. These specimens have very restrictive application ranges and are not suitable for general applications.

Furthermore, these conventional fixtures have a large contact area with the test specimen which allows for some of the test load to be transferred to the fixture itself resulting in an erroneous measurement of the coupon's compression strength in a nonconservative manner. Also, an opening must be cut into the fixture to allow for open and filled hole compression tests. This makes it difficult to perform measurements of strain in the vicinity of the opening. And furthermore, conventional fixtures cannot be easily modified for compression testing where it is desirable to support only one lengthwise extending edge of the test specimen.

Other conventional support devices have been disclosed. For example, U.S. Pat. No. 683,184 by Rockwell discloses a clamp having four rectangularly arranged blocks connected together in pairs by compression and expansion screws. In addition, U.S. Pat. No. 2,350,060 by Montgomery and U.S. Pat. No. 2,368,900 by Templin disclose compression testing devices for thin specimens wherein the devices each include a pair of T-shaped jaws having small diameter rollers to engage the side surfaces of the specimen. And, U.S. Pat. No. 4,840,070 by Ralfs et al discloses a laminate compression tester which includes a pair of adjustable stabilizing jaws having end segments which engage specimen grips of a testing machine.

SUMMARY OF THE INVENTION

The present invention pertains to apparatus for supporting an elongate workpiece between grips of a machine for compression testing of the workpiece. The apparatus includes grip plates for engaging opposing faces of the workpiece in a manner that the grip plates are engaged by the grips for delivering an axial force to the workpiece. In addition, the apparatus includes means for stabilizing the workpiece along first and second elongate sides of the workpiece. The stabilizing means includes (i) a first engaging surface for engaging a first face of the workpiece along an edge thereof at a location adjacent the first side and (ii) a second engaging surface for engaging a second face of the workpiece along an edge thereof at a location adjacent the first side, and a third engaging surface for engaging the second side of the workpiece.

In another embodiment, the apparatus includes grip plates for engaging opposing faces of the workpiece in a manner that the grip plates are engaged by the grips for delivering an axial force to the workpiece. In addition there are means for attaching the grip plates to the grips. The present embodiment also includes means for stabilizing the workpiece along first and second elongate sides of the workpiece. The stabilizing means includes (i) a first stabilizer plate having a recess for supporting the workpiece therein and (ii) a second stabilizer plate having a recess for also supporting the workpiece therein. Furthermore, there are means for connecting together the first and second stabilizer plates about the workpiece.

BRIEF DESCRIPTION OF THE DRAWINGS

These and other features of the present invention will be described in greater detail in the following Detailed Description in conjunction with the attached drawings, in which:

FIG. 1 is a side view of a conventional testing machine and conventional fixture for a test specimen;

FIG. 2 is an isometric view of the conventional specimen fixture shown in FIG. 1;

FIG. 3 is a plan view, of a conventional test specimen;

FIG. 4 is an isometric view of an exemplary specimen stabilizer of the present invention;

FIG. 5 is a side view of the stabilizer shown in FIG. 4;

FIG. 6 is a top view of the stabilizer shown in FIG. 4;

FIG. 7 is a side view of the stabilizer shown in FIG. 4;

FIG. 8 is another side view of the stabilizer shown in FIG. 4;

FIG. 13 is a plan view of a test specimen.

DETAILED DESCRIPTION

Figure 9:
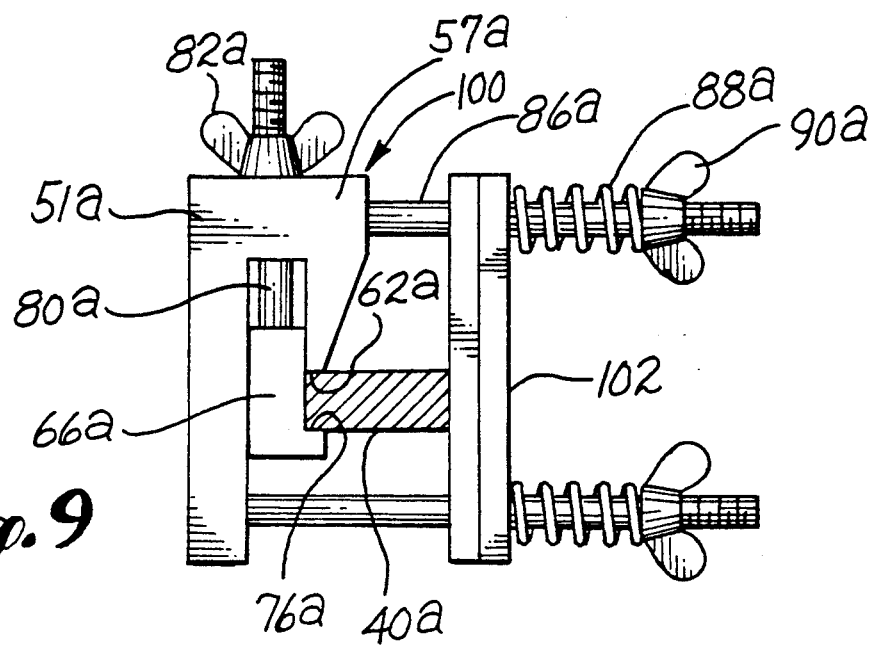
FIG. 9 is a top view of a second exemplary stabilizer of the present invention.

Before describing the present invention in greater detail, an additional brief description of a conventional test fixture and testing machine will be provided. Referring first to FIG. 1 there is shown a portion of a conventional compression/tension testing machine indicated at 20. In an exemplary embodiment, the testing machine 20 includes a model 647 hydraulic wedge grip which is part of an MTS 810 test system manufactured by MTS Corporation of Minneapolis, Minn. The testing machine 20 includes an upper wedge 22 having a pair of jaws (also referred to as "grips") 24 and a lower wedge 26 having a pair of grips 28. The grips 24, 28 are movable between a closed position (shown in FIG. 1) where the grips engage a conventional specimen fixture indicated at 30 and an open position (not shown) where the grips are spaced apart from the fixture 30.

As shown in FIGS. 1 and 2, the specimen fixture 30 includes an upper larger grip portion formed by identical left, right plates 32, 34 respectively, and a separate smaller, lower grip portion formed by identical left, right plates 36, 38, respectively. A specimen 40 (FIG. 3) having a rectangular plan configuration and a rectangular cross section is inserted between the left and right grip plates of the upper and lower grip portions and the opposing plates are then bolted together through openings 42 by bolts (not shown). The grip plates are bolted together to extend entirely across both faces of the specimen 40 and in a manner such that the upper and lower plates are vertically spaced apart from each other slightly by a gap 44. A hole 45 is made in one of the plates to allow for open and filled hole compression tests. Briefly, an open hole test involves a rectangular specimen having a circular center hole. The purpose of this test is to determine the influence of properties caused by a hole in the material. On the other hand, a filled hole test uses the same specimen as the open hole test except a fastener is installed in the hole prior to the test. This makes it difficult to obtain measurements of strain, etc. in the vicinity of the hole 45 because if the hole is made large enough to contain the necessary instrumentation to measure strain, there is a high probability of a buckling failure occuring from loss of support due to the opening.

With the presence of the gap 44, a slight movement together of the upper and lower portions of the testing machine is permitted in order to test the compression strength of the specimen 40 and to avoid reacting any of the compression loads through the fixture 30. In order to support the specimen 40 across the gap 44 and to prevent unwanted buckling of the specimen at the gaps, a lower blocking plate 46 is attached to the outer surface of the right grip plate 38 across the gap 44, and an upper blocking plate 48 is bolted to the outer surface of the upper left grip plate 32 across another gap 44.

Turning now to a first embodiment of the present invention, reference is made to FIGS. 4 through 8 where there is shown a stabilizer indicated at 50 (FIG. 4) formed by mirror image stabilizer sections 51 for stabilizing specimen 40. As shown best in FIG. 5, the specimen 40 is held in a vertical position at its top end between left, right grip plates 52 and at its bottom end between left right grip plates 54. The grip plates 52, 54 are grasped between upper grips 24 and lower grips 28 of the conventional testing machine 20 (shown in FIG. 1). As further shown in FIG. 5, the grip plates 52, 54, are spaced apart from and are not engaged by the stabilizer 50.

Each stabilizer section 51 includes a main frame having an L-shaped cross-section (FIG. 6) and formed by a large vertical outer wall 55, an opposing inner short wall 57 which is parallel to wall 52, and a top horizontal wall 56 which is joined to and ex between the tops of walls 55 and 57. It should be appreciated that the terms "vertical" and "horizontal" describe the relative positions of these elements in FIGS. 4 and 6 for the sake of convenience and clarity, and may not be descriptive of their actual positions during compression testing.

The inner wall 57 is further formed by a first vertical wall surface 59 (FIG. 4) which is opposite to an inner surface 58 of the outer wall 55. In addition, the inner wall 54 is formed by a second wall surface which includes an upper vertical portion and a lower surface portion 60 which slants downward and inward toward the opposing wall surface 59. The inner wall 57 is further formed by a narrow bottom gripping surface 62 which extends between the bottoms of surfaces 59, 60.

As shown in FIGS. 4 and 6, the bottom surface 62 of each stabilizer section 51 grips the top surface of the specimen 40 adjacent to lengthwise edge of the specimen. Due to the narrowness of the gripping surface 62, a small percentage of the top surface of the specimen is gripped by each stabilizer section 51.

In order to grip the bottom surface of the specimen 40, each stabilizer section 51 includes an elongate support bar 66 (FIG. 6) which is connected to the main frame of stabilizer 51. More specifically, the support bar 66 has a generally rectangular cross section with an inner vertical side surface 68 which is positioned flush against the opposing wall surface 59 and an outer vertical side surface 70 which is positioned flush against the wall surface 58. Furthermore, the side surface 68 extends downward below the upper gripping surface 62 and terminates at a ledge 74 which is formed by an narrow upper horizontal gripping surface 76 which is located directly below the upper gripping surface 62 and which has the same width as the width (distance between surfaces 59 and 60) of the upper gripping surface 62. In operation, the lower gripping surface 76 engages a narrow portion of the specimen's lower surface adjacent to the lengthwise edge of the specimen.

In order to attach each support bar 66 to the main frame of each stabilizer section 51, a pair of threaded studs 80 (FIG. 6) are mounted in the support bar 66 and extend upwardly from the support bar 66 and vertically through the wall 56. A pair of wing nuts 82 are tightened against the upper surface of the wall 56 to hold the support bar 66 in place. Furthermore, the left, right stabilizer sections 51 are joined together by four threaded studs 86 (FIG. 4) which are mounted in the right wall 52 and which extend leftwardly from the right wall through openings in the left wall 55. More specifically, two of the upper studs 86 extend horizontally through the upper horizontal wall 56 and the two lower studs 86 extend horizontally below the support bars 66.

In order to hold specimens having different widths, the left ends of the studs 86 have springs 88 mounted thereon and which are secured by wing nuts 90. In this manner, the distance between left, right faces 68 (FIG. 4) of the support bars 66 can be easily adjusted. The springs 88 allow the support bars to hold the specimen firmly without damaging the specimen from overtightening of the wing nuts. In a similar manner, specimens of different thicknesses may be accommodated in the holder 50 by readjusting the wing nuts 90.

As further shown in FIG. 8, there are gaps 92 between (i) the upper surfaces of the stabilizer sections 51 and the lower surface of the upper portion of the compression tester and (ii) the lower surfaces of the stabilizer sections 51 and the upper surface of the lower portion of the compression tester. As discussed previously, these gaps permits some vertical movement of the compression tester relative to the stabilizer 50. However, to prevent buckling of the specimen at the gaps 92, each grip plate 52, 54 includes a nose portion 94 which extends across the gap 92 while engaging the face of the specimen 40. More specifically, the nose 94 of the upper plate 52 is a flat, rectangular tab which extends vertically from the end of the plate 52 and which terminates prior to the connecting stud 86.

In operation, the specimen 40 is placed into the stabilizer and the wing nuts are adjusted to ensure a snug fit. Following this, the grip plates 52, 54 are manually held in place while the grips of the compression tester are closed against the plates 52, 54 at which time the specimen is ready for compression testing. During testing, the stabilizer 50 stabilizes the edges of the test specimen while the center section remains unsupported. Since the stabilizer only contacts the test specimen along a narrow band near its edges, the effects of friction between the holder and the specimen are minimized. This narrow contact area also minimizes the heat sink effect during environmental testing.

Figure 10:
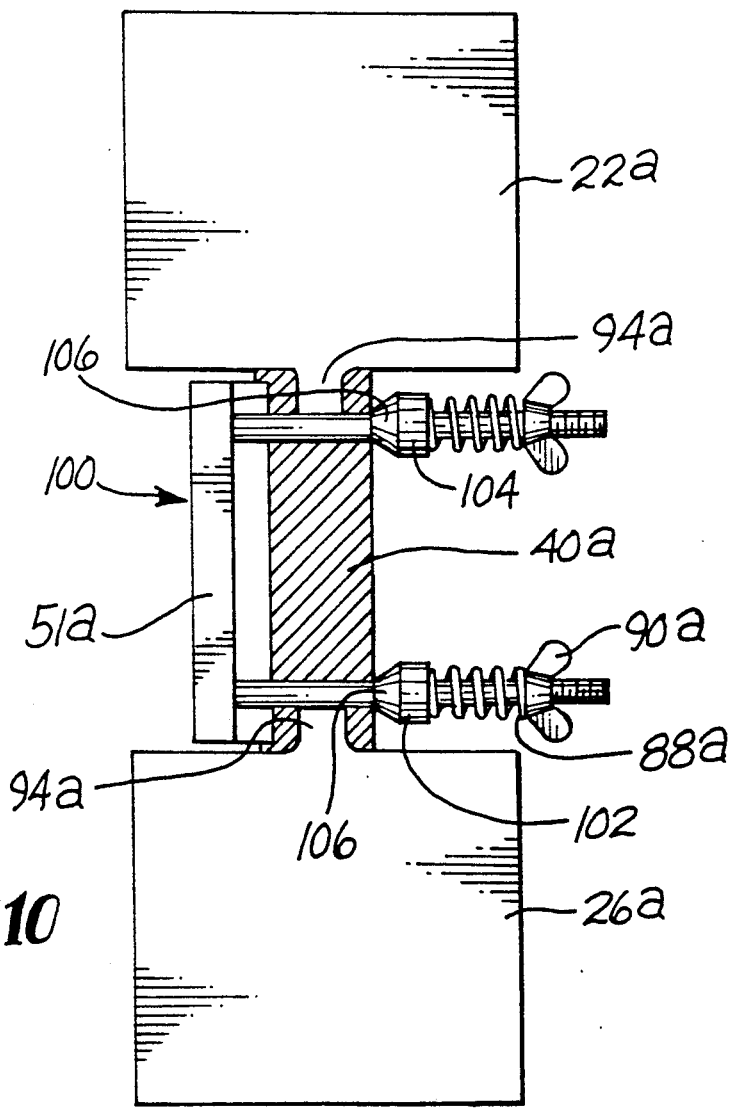
FIG. 10 is a side view of the exemplary stabilizer shown in FIG. 9.

Referring now to FIGS. 9 and 10, there is shown a second embodiment of the present invention which comprises a stabilizer, indicated at 100, for supporting the specimen 40 along only one of its lengthwise edges. In the present embodiment, like elements described in the previous embodiment will be assigned like numbers with the suffix "a" attached. In the present embodiment, the stabilizer 100 includes only one stabilizer section 51a. The stabilizer section 51a grasps one edge of the specimen 40a between the upper grasping surface 62a and the lower grasping surface 76a. In the present embodiment, the second stabilizer section 51 discussed with reference to FIGS. 4-8 is replaced by a pair of long and narrow vertical edge supports 102 which are mounted on the studs 86a opposite the inner wall 57 of the stabilizer section 51a. More specifically, each edge support 102 includes a rectangular base portion 104 (FIG. 10) which is connected to an integral triangular nose portion 106 which in turn engages a portion of the lengthwise edge of the specimen 40a opposite the edge engaged by the stabilizer section 51a. In this manner, the specimen 40a is held in position between the stabilizer section 51a and the edge supports 102. However, support against unwanted buckling during compression testing is provided only to the specimen edge supported by the stabilizer section 51a. The purpose of only supporting one edge of the specimen is to duplicate the loads which will be experienced by an actual part. That is, an actual part may experience loads along one edge (where it is attached to other structure) with the other edge being free (not attached to other structure) to buckle under actual operational conditions.

As further shown in FIG. 10, the upper edge support 102 which engages the edge of the specimen at a location opposite from the stabilizer section 51a slightly below the nose 94a of the upper grip plate. Similarly, the lower edge support 102 engages the edge of the specimen at a location opposite from the stabilizer section 51a slightly above the lower nose 94a of the lower grip plate.

Figure 11:
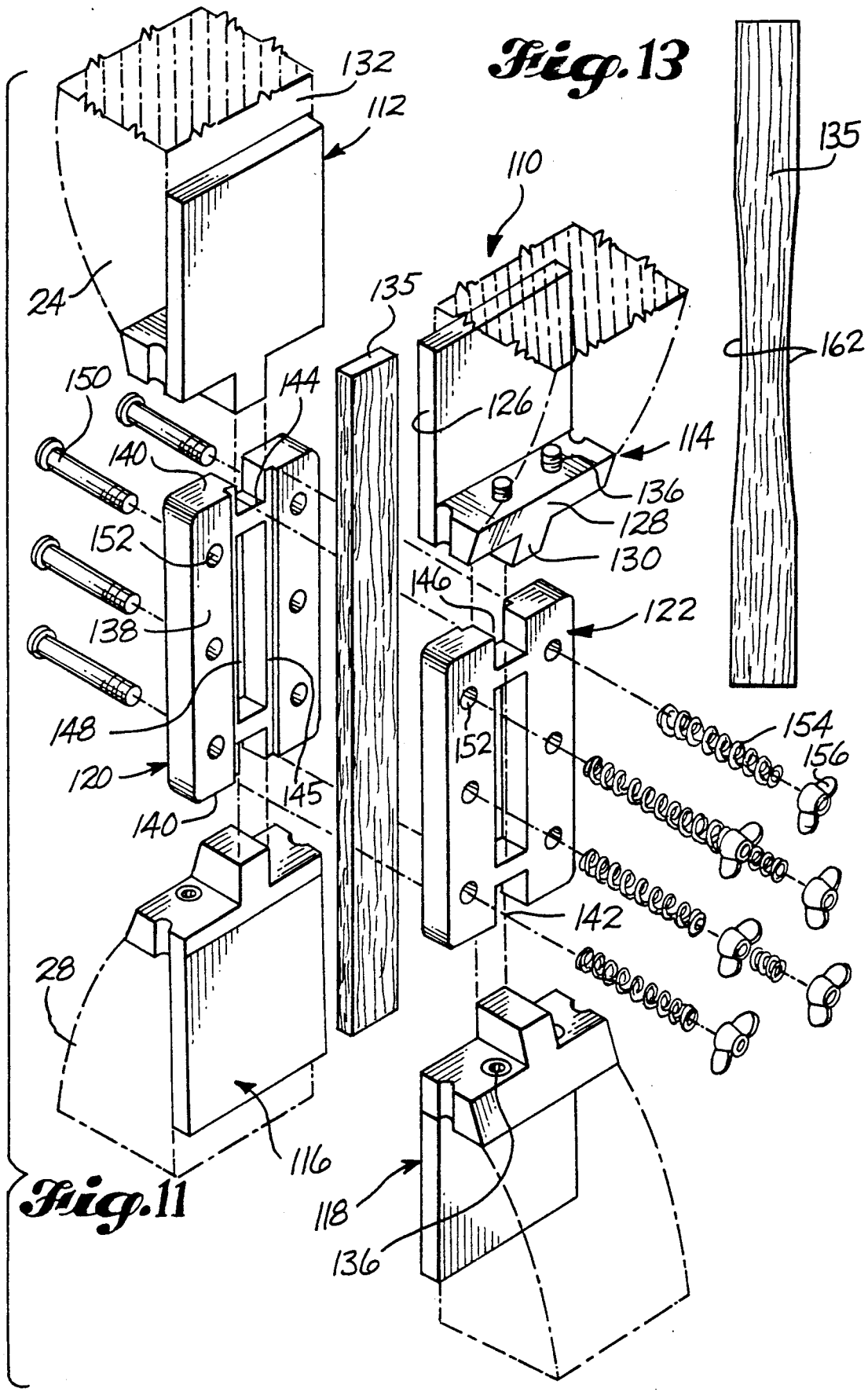
FIG. 11 is an exploded isometric view of another exemplary stabilizer of the present invention and a portion of a conventional test machine.
Figure 12:
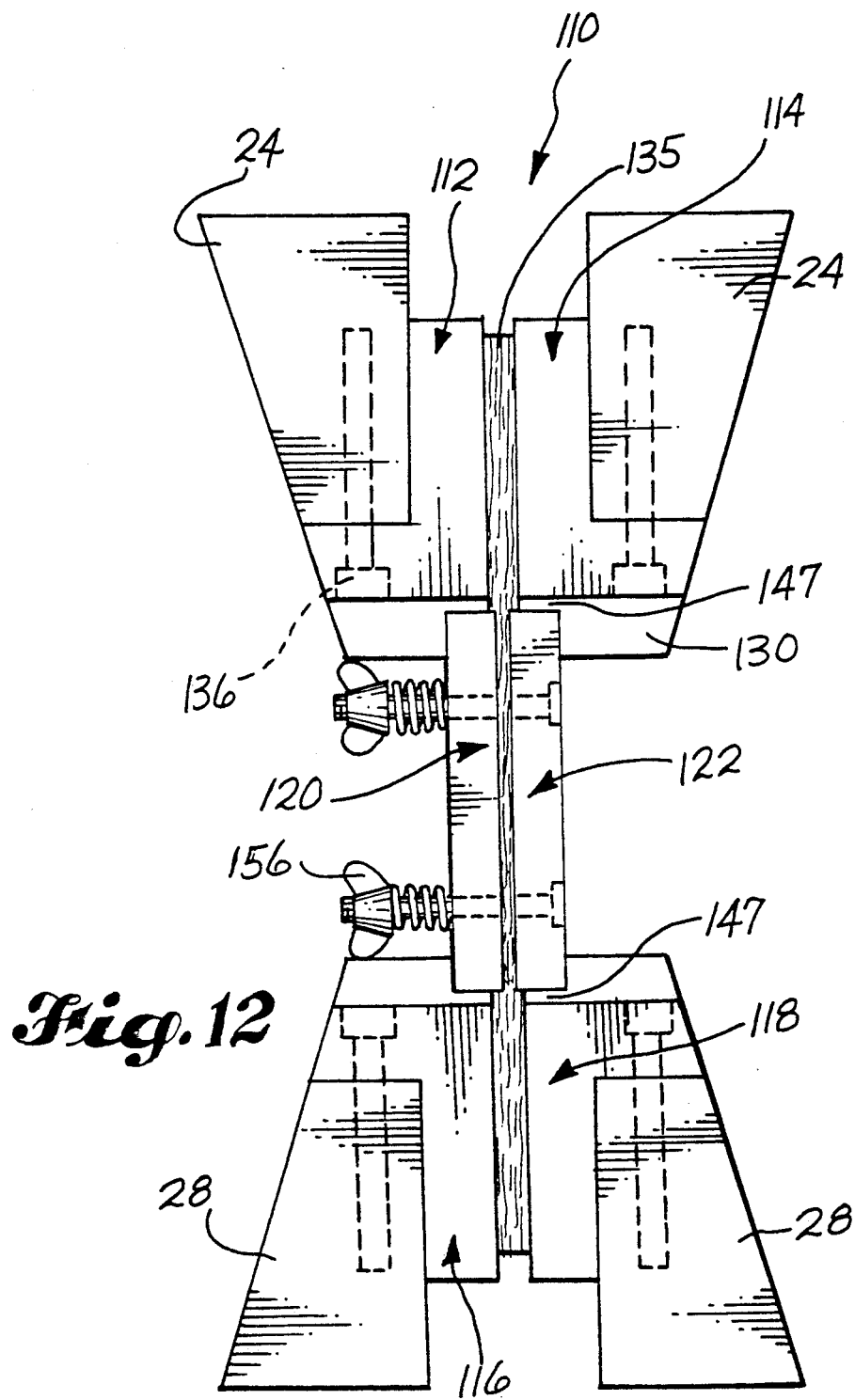
FIG. 12 is a side view of the stabilizer and the portion of the conventional test machine shown in FIG. 11.

Referring now to FIGS. 11 and 12 there is shown a stabilizer, generally indicated at 110, which is a third embodiment of the present invention. As shown in FIG. 11, the stabilizer 110 includes left, right upper grip plates indicated at 112, 114, respectively; left right lower grip plates indicated at 116, 118, respectively; and left, right stabilizer plates indicated at 120, 122, respectively. In the present embodiment, grip plates 112, 114, 116, and 118 are identical, and therefore only one will be described. Furthermore, stabilizer plates 120 and 122 are identical, and therefore only one will be described.

Referring first to FIG. 11, grip plate 114 has an L-shaped configuration including a vertical rectangular wall 26 and a generally rectangular flat base 128 mounted perpendicular to the bottom end of the wall 126. Furthermore, extending downward from the middle of the lower surface of the base 128 is a rectangular nose portion 130.

As further shown in FIG. 11 the grip plates are mounted to the grips 24, 28 of the compression testing machine. More specifically, the end of each machine grip has an L-shaped configuration including a horizontal surface (not shown) and a vertical surface 132 which join together at a corner 134. Each grip plate is mounted to its associated grip by screws 136 which extend vertically through openings in the base 128 on either side of the nose 130 and into the horizontal surface of the grip. In this manner, the grip plate is attached to the grip such that the vertical wall 126 of the grip plate is flush against the vertical surface 132 of the grip and the top surface of the grip plate base 128 is flush against the horizontal surface of the grip.

Stabilization of a test specimen 135 is accomplished by the stabilizer plates 120, 122. Each stabilizer plate has a generally rectangular configuration with an inner face 138 and upper and lower ends 140. The plate has a central longitudinal axis shown by a line designated by a number 142 extending between the upper and lower ends. In order to support the test specimen, each plate includes a recess 144 (located along the central axis 142) having a rectangular configuration which matches the general configuration of the specimen. The recess 144 includes narrow vertical ledges 145 at its opposite sides which engage the rear edges of the specimen. The depth of the recess 144 is much less than the thickness of the test specimen but is sufficient to support the specimen in the stabilizer plate and to provide stabilization. During testing, the specimen is held within the recesses 144 between the stabilizer plates.

In order to provide clearance for the grip plate noses 130 when the stabilizer is positioned on the testing machine, the upper and lower edges of each holder plate each include a rectangular notch 146. It should be appreciated that the stabilizer is mounted on the testing machine in a manner to provide gaps 147 (FIG. 12) between the stabilizer and the testing machine. Noses 130 extend across these gaps against the faces of the specimen to prevent unwanted buckling of the specimen during testing.

Furthermore, located between the notches 146 (FIG. 11) is elongate cutout 148 extending through the plate for attaching an extensometer to the specimen.

The stabilizer plates 120, 122 (FIG. 11) are connected together by bolts 150 which extend through holes 152 in the plates. In order to accommodate specimens having different thickness dimensions, springs 154 are mounted to the ends of the bolts against the outer face of the plate and are secured onto the bolts by wing nuts 156.

In this embodiment, compression testing of the specimen is relatively simple. Since the grip plates are mounted to the grips, it is necessary only to place the specimen between the stabilization plates, secure the stabilization plates together, then close the grips so that the free ends of the specimen (e.g., the ends not supported by the stabilization plates) are located between the grip plates.

There is shown in FIG. 13 a specimen 135 which is somewhat different from the specimen 40 discussed in previous embodiments. That is, opposing portions 162 of the lengthwise extending edges of the specimen extend inward in a concave manner. Historically, during tension testing of the specimen 40, there was a tendency for the specimen to fracture in the area of the grip plates due to stress concentration. By using the specimen 135, this tendency to fracture at the grip plates was eliminated. However, the specimen 135 was inappropriate for compression testing because of the absence of lengthwise support for the specimen when using conventional fixtures. This resulted in having to use the specimen 135 for tension testing and the specimen 40 for compression testing.

In the present embodiment, the specimen 135 can be used for both compression and tension testing. That is, the specimen 135 is supported along both edges by the recess ledges 145. More specifically, the distance from the widest portion of the specimen to the narrowest portion (at the middle of edge portion 162) is less than the width of ledge 145 so that full edge support is provided.

What is claimed is:

1. Apparatus for supporting an elongate workpiece between grips of a machine for testing of the workpiece, the apparatus comprising:
   a. grip plates for engaging opposing faces of the workpiece in a manner that the grip plates are engaged by the grips for delivering an axial force to the workpiece;
   b. means for stabilizing the workpiece along first and second elongate sides of the workpiece, the stabilizing means including (i) a first engaging surface for engaging a first face of the workpiece along an edge thereof at a location adjacent the first side and (ii) a second engaging surface for engaging a second face of the workpiece along an edge thereof at a location adjacent the first side, and a third engaging surface for engaging the second side of the workpiece.

2. Apparatus for supporting an elongate workpiece between grips of a machine for testing of the workpiece, the apparatus comprising:
   a. grip plates for engaging opposing faces of the workpiece in a manner that the grip plates are engaged by the grips for delivering an axial force to the workpiece;
   b. means for attaching the grip plates to the grips;
   c. means for stabilizing the workpiece along first and second elongate sides of the workpiece, the stabilizing means including (i) a first stabilizer plate having a recess for supporting the workpiece therein and (ii) a second stabilizer plate having a recess for supporting the workpiece therein; and
   d. means for connecting together the first and second stabilizer plates about the workpiece.

* * * * *